United States Patent [19]

Pang et al.

[11] Patent Number: 5,169,602

[45] Date of Patent: Dec. 8, 1992

[54] RESEALABLE CONDUIT AND METHOD

[75] Inventors: Wing S. Pang, Hacienda Heights, Calif.; Thomas L. Kraft; James W. Meador, both of Houston, Tex.

[73] Assignee: Beckman Instruments, Inc., Fullerton, Calif.

[21] Appl. No.: 490,051

[22] Filed: Mar. 7, 1990

[51] Int. Cl.⁵ .............................................. B65D 39/00
[52] U.S. Cl. ..................................... 422/103; 422/99; 422/100; 604/411; 222/83.5; 215/DIG. 3; 215/247; 215/260; 215/307; 73/863.81
[58] Field of Search ............... 422/99, 100, 103; 604/411; 222/83.5; 215/DIG. 3, 247, 260, 307; 73/863.81

[56] References Cited

U.S. PATENT DOCUMENTS

| | | | |
|---|---|---|---|
| 3,119,391 | 1/1964 | Harrison | 604/411 X |
| 3,460,702 | 8/1969 | Andrews | 215/247 |
| 3,849,070 | 11/1974 | Garza et al. | 436/133 |
| 3,930,413 | 1/1976 | Laird et al. | 73/863.85 |
| 4,020,837 | 5/1977 | Larson | 604/411 |
| 4,134,512 | 1/1979 | Nugent | 215/247 |
| 4,351,798 | 9/1982 | Marsoner et al. | 422/63 |
| 4,423,641 | 1/1984 | Ottung | 73/863.86 |
| 4,515,752 | 5/1985 | Miramanda | 422/99 |
| 4,537,593 | 8/1985 | Alchas | 604/411 |
| 4,808,381 | 2/1989 | McGregor et al. | 422/100 |
| 4,935,020 | 6/1990 | Brodén | 604/411 |

OTHER PUBLICATIONS

CleanTech Literature, "CleanTech System", Anonymous.
Helena Laboratories Literature Describing Tip Tops, 1988.

*Primary Examiner*—Robert J. Warden
*Assistant Examiner*—Stephanie Blythe
*Attorney, Agent, or Firm*—William H. May; Gary T. Hampson; Charles Berman

[57] ABSTRACT

A resealable conduit is used to remove or add fluid to a closed system without coring or contamination of the fluid. The conduit can include funnel-shaped guide means, duck bill valve means and beveled tip puncturing means. A conduit resting angle of less than about five degrees can be achieved. A tip bevel angle between about ten and twenty degrees is preferred. The beveled tip can have a rotated or twisted blade surface extension. A blade surface extension formed with a ninety degree rotation of the blade surface is preferred. Alternately, the puncturing means can include a needle point or a flat cutting surface.

32 Claims, 5 Drawing Sheets

RESEALABLE CONDUIT AND METHOD

BACKGROUND

The present invention is directed to a resealable conduit and method for removing or adding fluid to a closed system. The fluid can be of any type.

Physiological fluid samples in containers need to be easily accessible without compromising the integrity of the sample. Closed systems such as stoppered physiological fluid sample tubes are accessed to remove one or more aliquots of the fluid. Alternately, fluid can be added to the sample tube, such as when a dilution is desired. Various diagnostic and therapeutic tests can be performed upon the aliquots. Physiological fluids such as, for example, blood or urine are frequently collected and stored in sample tubes closed by a rubber or elastomeric material stopper.

Typically, fluid samples are removed from a stoppered tube by removing the stopper, inserting a pipette stem into the fluid, aspirating fluid into the pipette and replacing the stopper. This access method can create aerosols and exposes sample fluid to the local environment. Aseptic conditions can thereby be violated. Biohazard can arise when this prior art fluid access method is used if the sample tube contains virulent or infectious organisms. These problems are compounded when the sample tube is reaccessed to remove further fluid samples.

A further problem is coring, which can occur when a hollow conduit is inserted through a rubber or like-material stopper. Coring is the removal of stopper material from the wall of the stopper as a hollow conduit is forced through the stopper. The cored material can enter the bore of the conduit thereby blocking it. Additionally, cored material can fall into the sample fluid when insertion of the conduit is complete, thereby contaminating the sample and rendering it unsuitable for analysis.

Needle tip conduits for piercing rubber septums or stoppers are known. These devices suffer from the disadvantages of coring, lack of a closure valve to prevent fluid backflow when tipped or inverted, high cost and inability to maintain essentially aseptic conditions.

Accordingly, there is a need for a low cost stored in closed sample tubes without coring and with maintenance of a high level of fluid asepsis. The device and method should permit repeatable access to such body fluids with minimal risk of creating aerosols, biohazard or contamination of either sample fluid or the sampling environment.

SUMMARY

The present invention is directed to a low cost resealable conduit device and method which meets these needs. The resealable conduit can be inserted with little or no coring, through a rubber or like-material stopper of a fluid-containing sample tube. An elongated tubular member such as the stem of a pipette is inserted through the conduit to aspirate fluid. Alternately, fluid can be added by the pipette. The resealable conduit has closure means to prevent fluid backflow during normal handling, has re-entrant capability, is disposable, and minimizes risk of aerosol creation or contamination of a sample or the sampling environment.

A resealable conduit according to the present invention has guide means, puncturing means, and valve means. The guide means receives and guides the leading end of an elongated tubular member, such as a pipette stem, into the bore of the conduit. The guide means has a mouth into which the tubular member can be removably inserted. The puncturing means is used for puncturing a rubber or like-material stopper so that the conduit can be inserted through the stopper. The normally closed valve means is disposed in the conduit bore.

The mouth of the guide means can have a cross-sectional shape that is, for example, square, rectangular, circular, or elliptical. Preferably, the mouth of the guide means is circular or elliptical and the guide means is funnel-shaped.

The puncturing means preferably has a beveled tip to assist passage of the conduit through a stopper. The wall adjacent the leading edge of the bevel tip can be thickened for support. The leading edge can have a needle point or a flat puncturing surface. Alternately, the flat puncturing surface can be in the form of a blade surface extension.

Preferably, the valve means is a "duck bill" valve because such valves are easy to make, inexpensive and effectively provide the desired one way mechanical access while preventing fluid backflow.

The guide and puncturing means can be formed as parts of an integral conduit body or they can be formed separately and assembled. To provide structural support, a reinforcing rib can run vertically along the exterior of the conduit.

A preferred method for removing fluid from a closed system includes the steps of: inserting the beveled tip of a resealable conduit through a closure member of the system; inserting an elongated tubular member through the conduit; aspirating fluid into the tubular member; and withdrawing the tubular member from the conduit. The conduit can then close under valve action. This method can also include the additional step of scoring the top of the closure member before inserting the beveled tip through closure member to help prevent coring. A preferred method for adding fluid to a closed system is the same as that just recited, except that instead of aspirating fluid, fluid is dispensed through the tubular member.

An apparatus within the scope of the present invention for removing fluid from or adding fluid to a closed system can include a resealable conduit, an elongated tubular member, such as a pipette, a closure member, such as a rubber stopper, and any combinations thereof.

BRIEF DESCRIPTION OF THE DRAWINGS

These and other features, aspects, and advantages of the invention are illustrated by the following drawings.

DESCRIPTION

Figures 1, 2, 3, 4:
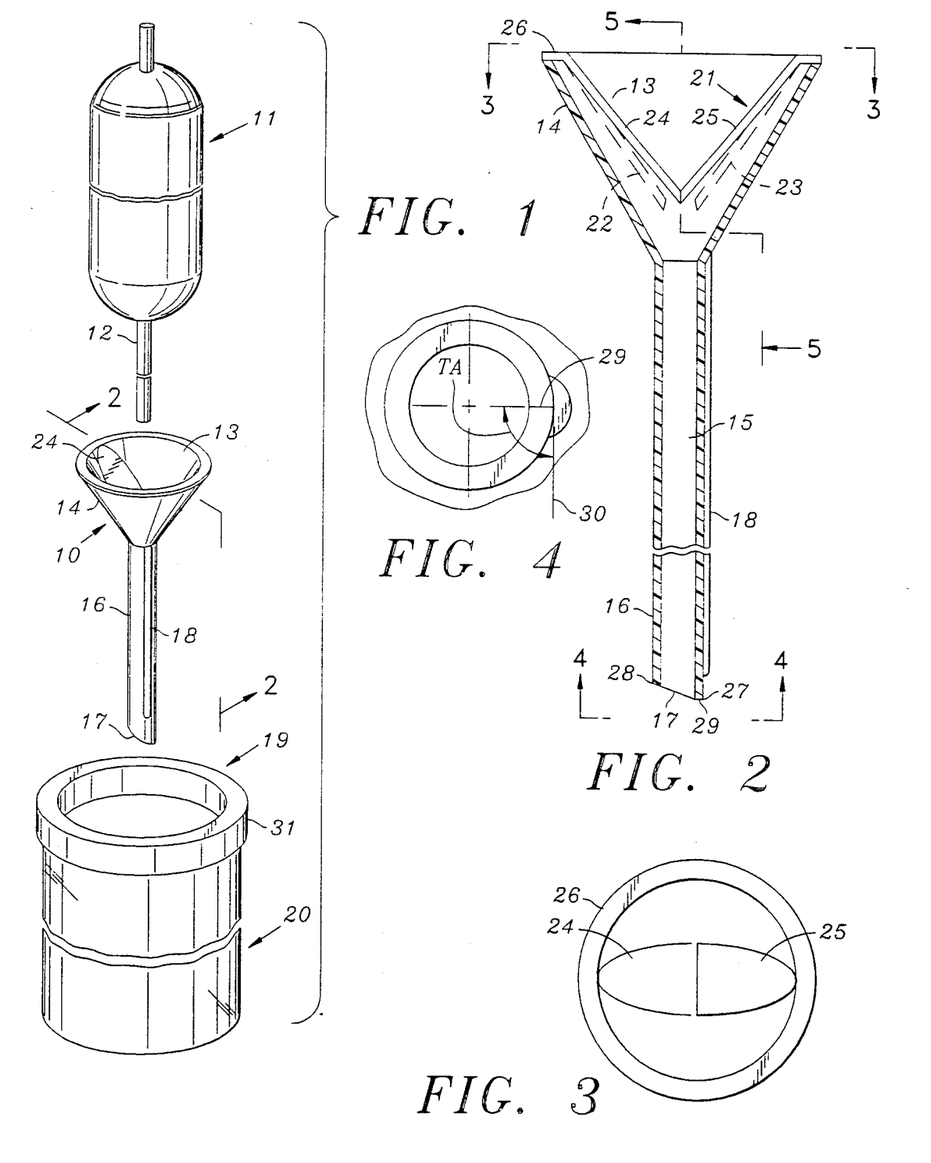
FIG. 1 is an exploded perspective view of a pipette, resealable conduit and stoppered sample tube.
FIG. 2 is a vertical, cross-sectional view of the resealable conduit taken along line 2—2 of FIG. 1.
FIG. 3 is a top plan view taken along line 3—3 of FIG. 2.
FIG. 4 is an enlarged bottom view taken along line 4—4 of FIG. 2.

FIG. 1 shows a resealable conduit 10, and a pipette 11 with elongated tubular member or stem 12 for insertion into, at a first end of the conduit, a mouth 13 of guide means 14. Pipette 11 can be a component of an automated fluid removal or addition apparatus. Alternately, pipette 11 can be operated manually. Conduit 10 has a bore 15 running the length of conduit 10. Bore 15 is wide enough for easy insertion and withdrawal of pipette stem 12. Bore 15 is wide at mouth 13 and narrower in cylindrical tube 16 of conduit 10. Tube 16 terminates at an end remote from guide means 14 in a second end.

The second end can have a beveled tip 17 to help reduce or prevent coring. Coring is believed to be a function of, at least, bevel angle (BA), stopper thickness and stopper material. The mouth 13 of guide means 14 can in horizontal cross-section be suitably square, rectangular, circular, elliptical or funnel-shaped, with tapered walls, as shown in FIG. 1, so that a pipette stem that is not directly centered over the long axis of the bore axis will upon contact with a wall of the guide means 14 be guided into the more narrow part of bore 15. This guiding feature is advantageous whether the resealable conduit is used in a manual operation or as part of an automated apparatus, such as a serum splitting instrument. Conduit 10 can have a reinforcing rib 18 running vertically along the exterior tube 16. Rib 18 functions to strengthen the tube to prevent cracking or buckling of conduit 10 when it is inserted through a closure means such as stopper 19 of sample test tube 20.

FIG. 2 shows that guide means 14 has valve means 21. Valve means 21 is a one-way closure device and prevents the backflow of fluid from sample tube 20. Valve means 21 is capable of opening and closing. Typically, the valve means can open, as shown by phantom lines 22 and 23 in FIG. 2, when pressure is applied to the outer face of the valve. The valve can close when the pressure is withdrawn and/or due to construction of the valve means from a self-sealing material, such as an elastomeric material. Any type of resealable closure means can be a suitable valve means. Valve means 21 can have at least two leaflets 24, 25 made of a resilient material that will reseal when pressure, as from the urging of pipette stem 12, is withdrawn. Thus, the leaflets normally rest against each other to close the valve. As shown in FIG. 3, leaflets 24 and 25 can taper towards one another. Periphery 26 of the leaflets can be fixed or sealed to guide means 14.

Valve 21 can be a "duck bill" valve (available from Vernay Europa B.V., P.0. Box 310, 875 Yellow Spring, Dayton, Ohio 45387). A duck bill valve is inexpensive, can be mechanically and/or chemically sealed to conduit 10 at valve periphery 26, and provides a one-way mechanical and/or fluid flow through conduit 10. Thus, entry into the resealable conduit is permitted in one direction, while not allowing fluid flow in the opposite direction. The duck bill valve can be made of a silicone rubber material to facilitate opening and closing of the leaflets.

Beveled tip 17 has a leading edge 27 and a trailing edge 28. Tip 17 can be integral with the rest of conduit 10 or can be constructed from a needle coated with a substance such as teflon and inserted into cylindrical tube 16. In one embodiment, the leading edge defines a flat cutting or puncturing surface 29. Cutting surface 29 is the first area of conduit 10 that comes into contact with the stopper 19.

FIG. 4 illustrates twist angle (TA). Twist angle is the angle of rotation of the cutting edge. Twist angle can be described as the angle formed between a cutting surface 29 and a tangent 30. Tangent 30 is drawn from the exterior of conduit 10 adjacent cutting surface 29. Thus, twist angle is the angle from tangent 30 through which cutting surface 29 is twisted or rotated during formation of the puncture means. Twist angle is between about 0° and about 180° to help prevent coring of the stopper, reduce the required puncture force, and help prevent excess tearing of the stopper during puncturing. Preferably, twist angle is about 90° so as to help minimize the amount of coring, puncture force and stopper tearing.

Figure 5:
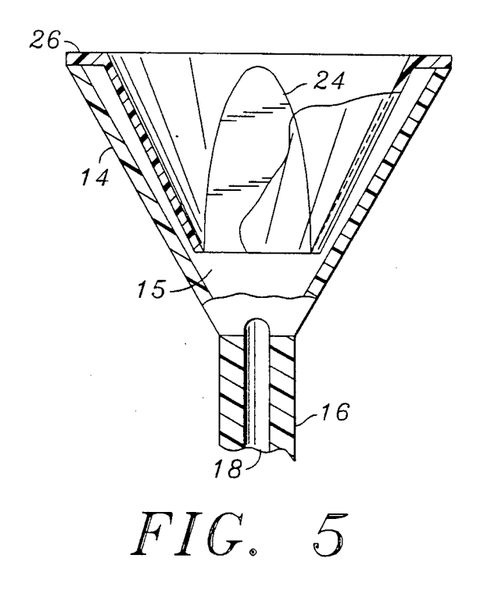
FIG. 5 is a fragmentary, vertical, side cross-sectional view taken along line 5—5 of FIG. 2.
Figure 6:
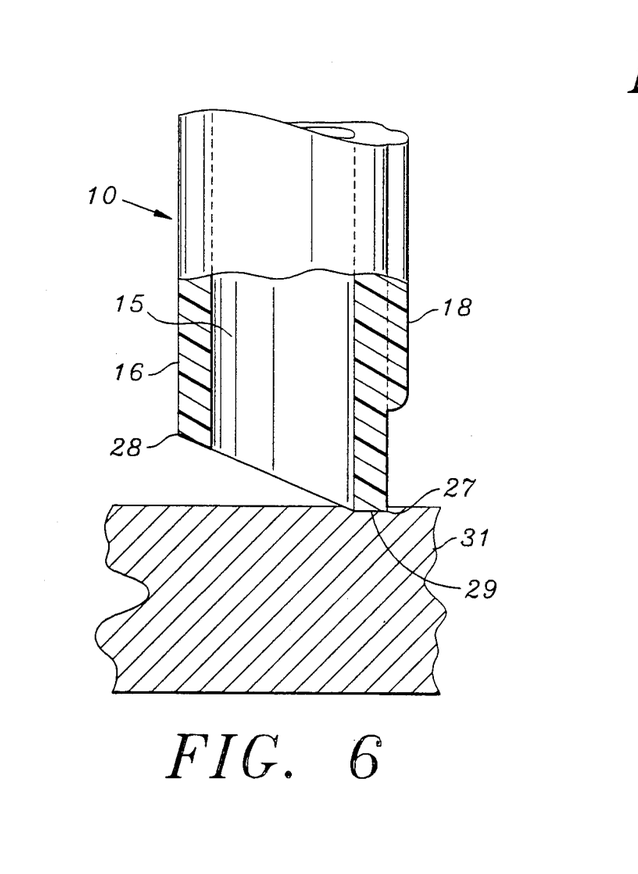
FIG. 6 is a fragmentary, vertical, cross-sectional view illustrating initial piercing contact by the resealable conduit.
Figure 7:
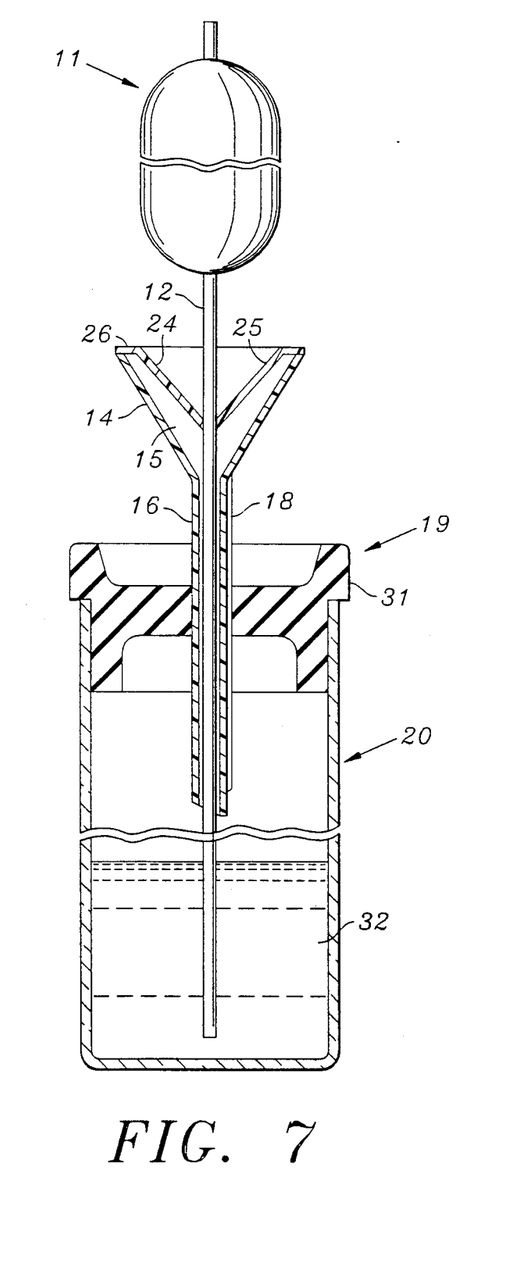
FIG. 7 is a vertical, cross-sectional view of the resealable conduit in use.

FIG. 5 shows another view of the guide means 14 and upper part of the tube 16 of the conduit illustrated in FIG. 2. FIG. 6 shows the initial piercing contact of cutting edge 29 into the rubber or rubber-like material 31 of stopper 19. FIG. 7 shows conduit 10 in use with a pipette stem 12 inserted therethrough.

Figure 8:
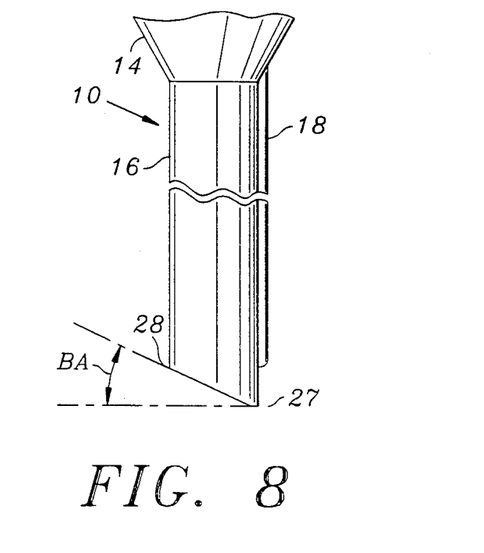
FIG. 8 is a side elevational view of the resealable conduit illustrating bevel angle.

FIG. 8 illustrates bevel angle (BA). Bevel angle is the angle between a tangent from the leading edge and the trailing edge of a beveled tip. Coring of a rubber or elastomeric closure means is reduced when bevel angle is greater than about 0° and less than about 75°, with minimal or no coring occurring when the bevel angle is between about 10° and about 20°. Preferably, therefore, the conduit has a bevel with a bevel angle between about 10° to about 20°.

Figure 9:
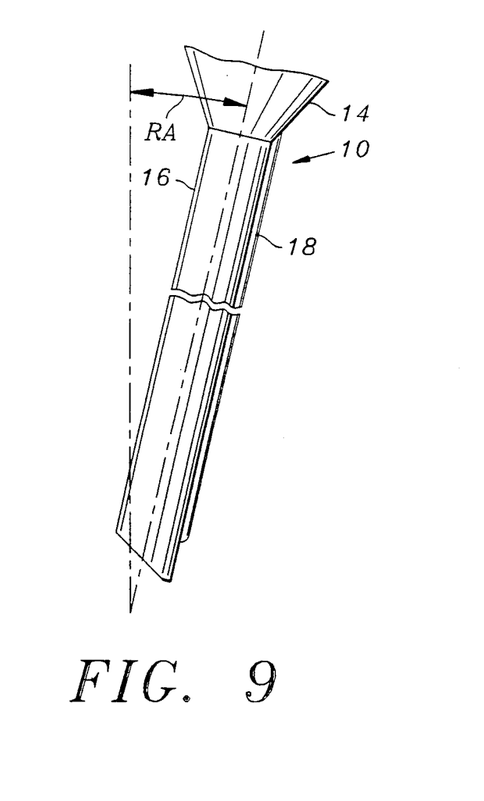
FIG. 9 is a side elevational view of the resealable conduit illustrating resting angle.
Figure 10:
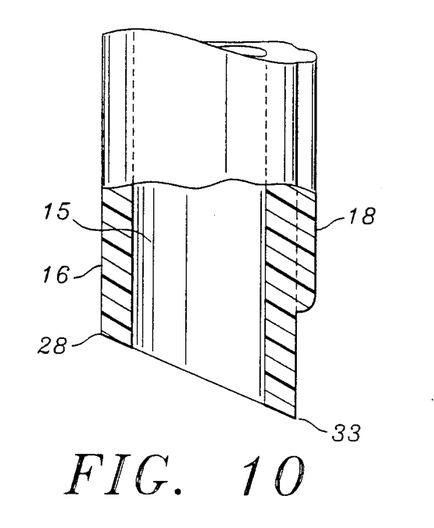
FIG. 10 is a fragmentary, vertical, cross-sectional view of an alternate form of the bevel tip.

The bevel angle influences the resting angle (RA). FIG. 9 illustrates resting angle. It was found that simple bevels, wherein the leading and trailing edges are joined by a straight line, gave little or no coring and a low resting angle. Preferably, the bevel is a simple bevel. Resealable conduits with bevel angles of between 10° to about 20° were found by Applicants to have the lowest resting angles. Resting angle is the angle insertion of conduit 10 through a stopper. Upon insertion through a stopper, the conduit should assume as nearly a vertical position as possible, that is, have a low resting angle, so that when a pipette stem is inserted through the conduit, the stem will not impact the wall of the sample tube. Preferably, therefore, the resting angle is less than about 20°, such as 10°, 5° or even about 0°. Low resting angle can assist low friction access of a pipette stem to fluid within a sample tube.

Figures 15, 16:
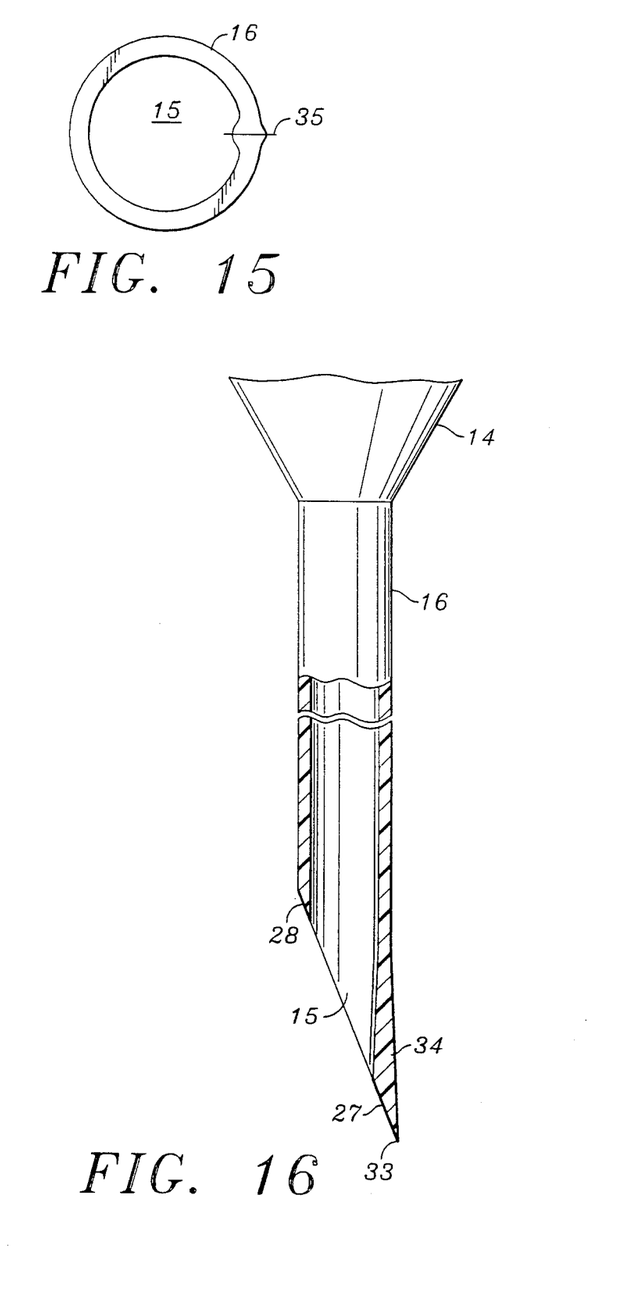
FIG. 15 is a bottom view taken along line 15—15 of FIG. 14.
FIG. 16 is a fragmentary, side elevational, cross-sectional view of a further embodiment of the bevel tip.

FIG. 16 shows another embodiment of the invention. Tip 17 can have a leading edge 27 with a cutting surface 29 terminating in a needle point 33. A puncturing, needle tip is easy to construct and gives little or no coring.

Optionally, conduit wall 34 adjacent puncturing needle 33 can be thickened to provide support.

Figure 14:
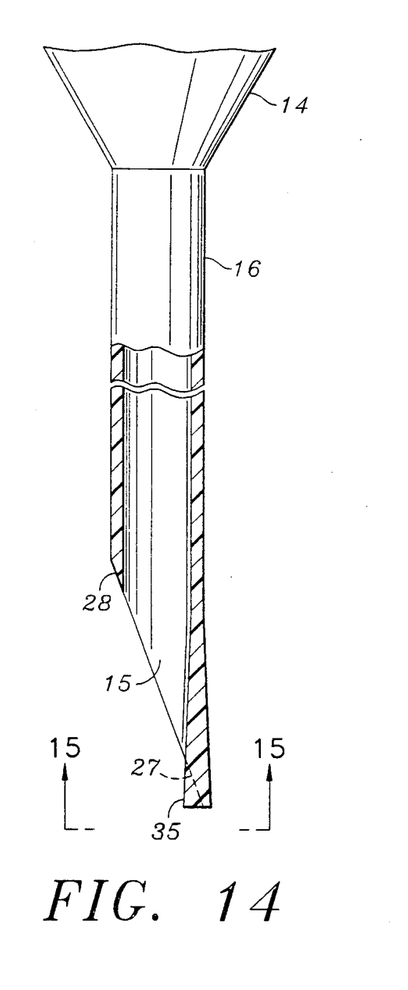
FIG. 14 is a fragmentary, side elevational, cross-sectional view of a further alternate form of the bevel tip.

In yet another embodiment, as shown in FIGS. 14 and 15, cutting edge 29 can be a blade surface extension 35. Blade surface extension 35 can have a twist angle of between about 0° and less than about 180°. Preferably, the twist angle of blade surface extension 35 is about 90°, for the reasons given previously. Extension 35 can blend into the structure of the cylindrical tube 16; that is, extension 35 tapers to nothing along the longitudinal axis of the conduit.

Figure 11:
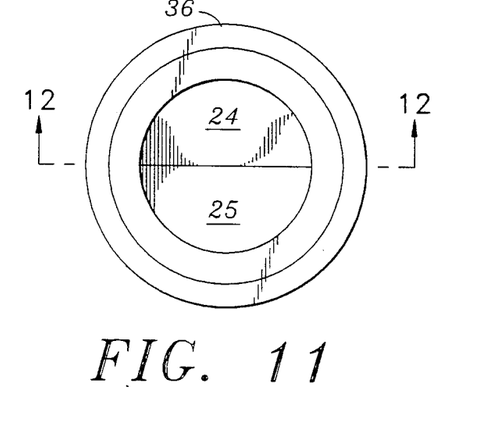
FIG. 11 is a top plan view of an alternate form of the guide means.
Figure 12:
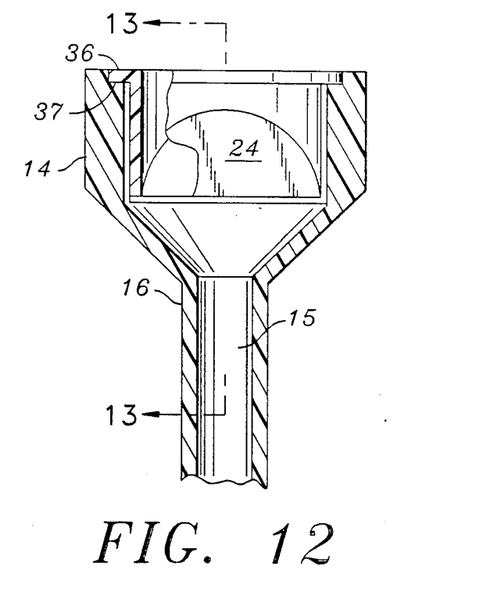
FIG. 12 is a fragmentary, vertical, cross-sectional view taken along line 12—12 of FIG. 11.
Figure 13:
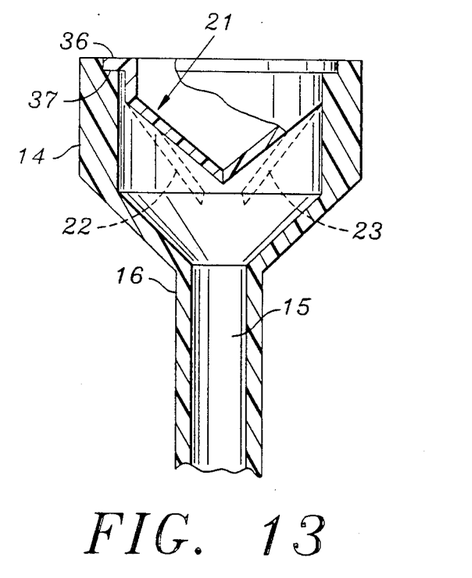
FIG. 13 is a vertical, cross-sectional view taken along line 13—13 of FIG. 12.

FIGS. 11, 12 and 13 show additional embodiments of the guide means 14 and valve means 21. A circular lip 36 of valve means 21 is joined to a mating circular flange 37 formed from the wall of guide means 14. Flange 37 can be adjacent the mouth of the guide means.

Conduit 10 can be of any suitable size depending upon parameters such as stopper material, stopper diameter, pipette stem length and diameter, etc. Conveniently, conduit 10 can be approximately ¼ to ⅜ inch in inside diameter at mouth 13, and decrease uniformly in diameter to approximately ⅛ inch in inside diameter at tube 16. Tube 16 can be about one inch in length with a wall thickness of about 1/16 inch.

Conduit 10 can be thermoformed from an acetyl or other thermoplastic which will permit molding of sharp , edges at the beveled tip, which will remain sharp over time. The conduit can be made from a styrene such as ABS (acrylongitrile butadiene styrene).

Conduit 10 is inserted through a stopper 19 by puncturing stopper 19 with the beveled tip 17 of conduit 10. Pipette stem 12 is then inserted through the duck bill valve of conduit 10 and fluid 32 is aspirated from tube 20 into the pipette. Alternately, fluid can be dispensed into the sample tube from the pipette. Finally, pipette stem 12 is withdrawn from conduit 10. Duck bill valve 21 provides reentrant capability.

To help prevent coring of the cap, the cap can be scored before puncture by the conduit. Scoring involves the marking or "scoring" of the stopper with a sharp object. The cut or shallow slit thereby made in the cap stopper can assist initial puncturing by the conduit and also assist passage of the conduit through a cap stopper without coring.

In use, resealable conduit 10 is positioned over the top of a conventional physiological fluid collection tube 20. Tube 20 can contain any of a variety of physiological or nonphysiological fluids. As tube 20 is either brought to the conduit 10 or conduit 10 is brought to tube 20, tip 17 contacts the top of stopper 19.

The present invention also includes within its scope an apparatus comprising a conduit 10, pipette 11 and a sample tube stopper 19 or any combination of these components, with or without insertion of the conduit 10 through the stopper 19.

Any septum-type closures that can be pierced to gain access to a closed system on a repeatable and resealable basis are suitable for the present conduit 10. The resealable conduit renders unnecessary removal of the stopper of a sample tube to access fluid contained by the stoppered tube. The conduit allows essentially aseptic removal of fluid on a repeatable basis. The present invention is inserted through a stopper and remains, in part, exterior to the stopper.

The disclosed resealable conduit can be used manually or as part of an automated procedure. In a manual operation, the user presses the puncture means through the septum of a closed system, followed by insertion of a tubular member into the conduit. Fluid can be added to or removed from the closed system through the tubular member, typically a pipette stem.

Alternately, or in conjunction with one or more manually effected steps, the puncture means of the conduit can be inserted through the septum or stopper in a machine-assisted step. When used in an automated procedure, the tubular member can be a pipette or a probe component of a stand-alone or workstation instrumentation. For example, the resealable conduit can be used in conjunction with the Beckman Synchron Clinical Analyzers, such as the Beckman CX-5.

Significant advantages of the invention include:

1. Non-coring penetration of a rubber or like-material stopper by the conduit;
2. A conduit that is resealable, with one-way mechanical access and that prevents fluid backflow;
3. Re-entrant conduit capability;
4. Low-friction access to sample by a pipette or other tubular member;
5. Disposable, resealable conduit;
6. Essentially biohazard-free operator interaction; and
7. Essentially biohazard-free serum (or other physiological or nonphysiological fluid) transfer.

The resealable conduit provides a solution to the problem of aseptically violating the cap of a sample tube in order to repeatably remove fluid, such as a physiological fluid from the tube without the creation of aerosols, biohazards or exposing the blood products to the exterior environment without containment. The conduit is constructed inexpensively so as to be a disposable device.

Although several embodiments of the invention have been disclosed, it should be understood that the present invention is in no way limited thereby and that its scope is to be determined by the appended claims.

We claim:

1. A resealable conduit, comprising:
   (a) a conduit bore having first and second ends;
   (b) a funnel-shaped guide means being a mouth at the first end of the conduit bore for receiving and guiding a leading end of an elongated tubular member;
   (c) puncturing means at the second end of the conduit bore;
   (d) valve means disposed within the guide means, the valve means having an upper portion and a lower portion and having a continuous and integral funnel-shaped cross-section which is substantially similar to the funnel-shaped cross-section of the guide means and comprising a plurality of movable leaflets, the leaflets being made of resilient material, the leaflets extending inwardly from the mouth of the guide means, and the leaflets having ends remote from the mouth, the ends being in point to point engagement to close the valve means and point to point non-engagement to open the valve means and wherein the valve means at its lower portion does not rest on the conduit bore, and the leaflets are movable between the open and closed positions without engaging the conduit bore; and
   (e) the guide means being wider than the bore at the second end, and the guide means being directed so that the leading end of the elongated tubular member is removably insertable through the valve means.

2. The resealable conduit as claimed in claim 1, wherein the guide means and puncturing means are an integral body.

3. The resealable conduit as claimed in claim 1, wherein the guide means and puncturing means are separable.

4. The resealable conduit as claimed in claim 1, wherein the mouth includes a cross-section selected from the group consisting of square, rectangular, circular and elliptical.

5. The resealable conduit as claimed in claim 1, wherein the guide means has uniformly sloping walls that taper inward from the mouth.

6. The resealable conduit as claimed in claim 1, wherein the puncturing means includes a beveled tip, the beveled tip having a leading edge and a trailing edge.

7. The resealable conduit as claimed in claim 6, wherein the wall of the leading edge is thicker than the wall of the trailing edge.

8. The resealable conduit as claimed in claim 6, wherein the leading edge has a needle point.

9. The resealable conduit as claimed in claim 6, wherein the leading edge has a blade surface extension beyond the beveled tip.

10. The resealable conduit as claimed in claim 9, wherein the blade surface extension has a nonzero twist angle.

11. The resealable conduit as claimed in claim 10, wherein the twist angle is greater than about 0° and less than about 180°.

12. The resealable conduit as claimed in claim 10, wherein the twist angle is about 90°.

13. The resealable conduit as claimed in claim 6, wherein the bevel angle of the beveled tip is greater than about 0° and less than about 75°.

14. The resealable conduit as claimed in claim 6, wherein the bevel angle is between about 10° and about 20°.

15. The resealable conduit as claimed in claim 1, wherein the valve means is fixed to the guide means.

16. The resealable conduit as claimed in claim 1, wherein the valve means is a duck bill valve.

17. The resealable conduit as claimed in claim 16, wherein the duck bill valve comprises two leaflets.

18. The resealable conduit as claimed in claim 1, wherein the valve means includes a circular lip at a mouth of the guide means and two leaflets made of a resilient material extending inwardly from the lip, the lip being affixed to a mating circular flange about the guide means.

19. The resealable conduit as claimed in claim 18, wherein the flange is adjacent to and about the mouth of the guide means.

20. The resealable conduit as claimed in claim 1, wherein the bore includes a cylindrical tube, the tube joining the guide means to the puncturing means.

21. The resealable conduit as claimed in claim 20, wherein the tube further includes a reinforcing rib.

22. The resealable conduit as claimed in claim 1, wherein the guide means and the puncturing means are made of a thermoplastic substance.

23. The resealable conduit as claimed in claim 1, wherein the valve means is constructed of a self-sealing elastomeric material.

24. A resealable conduit, comprising:

(a) funnel-shaped guide means at a first end of a conduit bore for receiving and guiding a leading end of the tubular member;

(b) a duck bill valve, the valve having a circular lip at a mouth of the guide means and two leaflets made of a resilient material and extending inwardly from the lip, the lip being affixed to a mating circular flange about the guide means, and the leaflets having ends remote from the mouth, the ends being in point to point engagement to close the valve and point to point non-engagement to open the valve and wherein there is a space between the conduit bore and guide means, on the one hand, and the leaflets on the other hand such that the space communicates with the conduit bore, and wherein the valve at its lower portion does not rest on the conduit bore, and the leaflets being movable in the space between the open and closed positions; and (c) a beveled tip at a second end of the conduit bore, the beveled tip having a leading edge and a trailing edge.

25. The resealable conduit as claimed in claim 24, wherein the valve is made of a silicone rubber.

26. The resealable conduit as claimed in claim 24, wherein the valve includes leaflets made of a self-sealing elastomeric material, the leaflets resting against each other to close the valve, and the leaflets being capable of being separated by the urging of an elongated tubular member thereby opening the valve and allowing passage therethrough of the tubular member, and wherein withdrawal of the tubular member allows the leaflets to close to thereby reseal the valve.

27. A resealable conduit having a bore for receiving an elongated tubular member, the conduit having been inserted through a stopper for a physiological fluid sample tube, the resealable conduit comprising:

(a) funnel-shaped guide means having a mouth at a first end of a conduit bore for receiving an elongated tubular member, the guide means including uniformly sloping walls that taper inward from the mouth;

(b) a beveled tip at a second end of the conduit bore for insertion through the stopper, the beveled tip having a leading edge and a trailing edge, the bevel angle being between about 10° and about 20°; and (c) a duck-bill valve means disposed within the guide means, the valve means having an upper portion and a lower portion and having a continuous and integral funnel-shaped cross-section which is substantially similar to a funnel-shaped cross-section of the guide means and comprising a plurality of movable leaflets, the leaflets being made of resilient material, the leaflets extending inwardly from the mouth of the guide means, and the leaflets having ends remote from the mouth, the ends being in point to point engagement to close the valve means and point to point non-engagement to open the valve means and wherein there is a space between the conduit bore and guide means, on the one hand, and the leaflets on the other hand such that the space communicates with the conduit bore, and wherein the valve means at its lower portion does not rest on the conduit bore, and the leaflets being movable in the space between the open and closed positions, and whereby the elongated tubular member is removably insertable into the first end, through the valve means, and into a sample tube and fluid is prevented from escaping from the sample tube after the withdrawal of the elongated tubular member.

28. The resealable conduit as claimed in claim 27, wherein the resting angle between a vertical line and the axis of the conduit inserted through the stopper is less than about 20°.

29. The resealable conduit as claimed in claim 27, wherein the resting angle is less than about 10°.

30. The resealable conduit as claimed in claim 27, wherein the resting angle is less than about 5°.

31. Apparatus for removing fluid from or adding fluid to a closed system, comprising:
  (a) a resealable conduit having a bore for receiving an elongated tubular member, the resealable conduit including:
    (i) a funnel-shaped guide means to receive and guide a leading end of the tubular member,
    (ii) puncturing means at a second end of the bore, and
    (iii) valve means disposed within the guide means, the valve means having an upper portion and a lower portion and having a continuous and integral funnel-shaped cross-section which is substantially similar to the funnel-shaped cross-section of the guide means and comprising a plurality of movable leaflets, the leaflets being made of resilient material, the leaflets extending inwardly form the mouth of the guide means, and the leaflets having ends remote from the mouth, the ends being in point to point engagement to close the valve means and point to point non-engagement to open the valve means and wherein there is a space between the conduit bore and guide means, on the one hand, and the leaflets on the other hand such that the space communicates with the conduit bore, and wherein the valve means at its lower portion does not rest on the conduit bore, and the leaflets being movable in the space between the open and closed positions; and
  (b) a closure member capable of closing a fluid-containing system,
  whereby the resealable conduit is adapted for location within a closure member of a closed system so that a leading end of the elongated tubular member is removably insertable through the valve means to thereby permit removal or addition of fluid.

32. Apparatus for removing fluid from or adding fluid to a stoppered physiological fluid sample tube, comprising:
  (a) a resealable conduit having a bore for a pipette for aspirating or dispensing fluid with a sample tube, the resealable conduit including:
    (i) funnel-shaped guide means to receive and guide a leading end of the pipette,
    (ii) puncturing means at a second end of the bore, and
    (iii) valve means disposed within the guide means, the valve means being capable of opening and closing, the valve means having an upper portion and a lower portion and having a continuous and integral funnel-shaped cross-section which is substantially similar to the funnel-shaped cross-section of the guide means and comprising a plurality of movable leaflets, the leaflets being made of resilient material, the leaflets extending inwardly from the mouth of the guide means, and the leaflets having ends remote from the mouth, the ends being in point to point engagement to close the valve means and point to point non-engagement to open the valve means and wherein there is a space between the conduit bore and guide means, on the one hand, and the leaflets on the other hand such that the space communicates with the conduit bore, and wherein the valve means at its lower portion does not rest on the conduit bore, and the leaflets being movable in the space between the open and closed positions; and
  (b) a rubber or like-material stopper capable of closing a physiological fluid sample tube,
  whereby the resealable conduit is inserted through the stopper and the stem of the pipette is removably insertable through the valve means to thereby permit aspiration or adding of fluid.

* * * * *

UNITED STATES PATENT AND TRADEMARK OFFICE
CERTIFICATE OF CORRECTION

PATENT NO.   : 5,169,602
DATED        : Dec. 8, 1992
INVENTOR(S)  : Pang, et al.

It is certified that error appears in the above-identified patent and that said Letters Patent is hereby corrected as shown below:

Column 1, line 45

Reads:   "Accordingly, there is a need for a low cost stored in closed sample..."

Should read:   "Accordingly, there is a need for a low cost resealable conduit and method for accessing body fluids stored in closed sample..."

Column 4, line 55

Reads:   "Resting angle is the angle insertion of conduit 10..."

Should read:   "Resting angle is the angle between a vertical line and the axis of bore 15 after insertion of conduit 10..."

Signed and Sealed this

Sixteenth Day of November, 1993

Attest:

BRUCE LEHMAN

*Attesting Officer*     *Commissioner of Patents and Trademarks*